United States Patent
Dai et al.

(10) Patent No.: US 10,527,849 B2
(45) Date of Patent: Jan. 7, 2020

(54) AUGMENTED REALITY VEHICULAR ASSISTANCE FOR COLOR BLINDNESS

(71) Applicant: TOYOTA JIDOSHA KABUSHIKI KAISHA, Toyota-shi, Aichi-ken (JP)

(72) Inventors: Siyuan Dai, Mountain View, CA (US); Nikos Arechiga, Mountain View, CA (US); Chung-Wei Lin, Mountain View, CA (US); Shinichi Shiraishi, Mountain View, CA (US)

( * ) Notice: Subject to any disclaimer, the term of this patent is extended or adjusted under 35 U.S.C. 154(b) by 0 days.

(21) Appl. No.: 15/653,342

(22) Filed: Jul. 18, 2017

(65) Prior Publication Data

US 2019/0025584 A1   Jan. 24, 2019

(51) Int. Cl.
| | |
|---|---|
| G02B 27/01 | (2006.01) |
| A61F 9/08 | (2006.01) |
| G02B 5/32 | (2006.01) |
| G06F 3/00 | (2006.01) |
| G06T 19/00 | (2011.01) |

(52) U.S. Cl.
CPC ............. *G02B 27/017* (2013.01); *A61F 9/08* (2013.01); *G02B 5/32* (2013.01); *G02B 27/01* (2013.01); *G02B 27/0101* (2013.01); *G06F 3/005* (2013.01); *G06T 19/006* (2013.01); *G02B 2027/014* (2013.01); *G02B 2027/0112* (2013.01); *G02B 2027/0141* (2013.01); *G02B 2027/0178* (2013.01); *G02B 2027/0185* (2013.01)

(58) Field of Classification Search
None
See application file for complete search history.

(56) References Cited

U.S. PATENT DOCUMENTS

| | | | |
|---|---|---|---|
| 8,497,880 B2 * | 7/2013 | Victor | B60Q 9/008 |
| | | | 345/660 |
| 8,831,849 B2 | 9/2014 | Joshi et al. | |
| 9,373,046 B2 | 6/2016 | Nelson | |

(Continued)

FOREIGN PATENT DOCUMENTS

| | | |
|---|---|---|
| JP | 2008-094377 | 4/2008 |
| JP | 2009-099060 | 5/2009 |

(Continued)

OTHER PUBLICATIONS

JPO, Notice of Reason for Rejection for Japanese Patent Application No. 2018-119182, dated May 21, 2019, 3 pages.

(Continued)

*Primary Examiner* — Parul H Gupta
(74) *Attorney, Agent, or Firm* — Burbage Law, P.C.; Jon-Michael Burbage; Elizabeth Ruzich

(57) ABSTRACT

The disclosure includes embodiments for providing augmented reality ("AR") vehicular assistance for drivers who are colorblind. A method according to some embodiments includes identifying an illuminated light in a driving environment of a vehicle that includes an AR headset. The method further includes determining a vehicular action to be taken responsive to the illuminated light being identified in the driving environment of the vehicle. The method further includes displaying an AR overlay using the AR headset that visually depicts a word which describes the vehicular action to be taken responsive to the illuminated light being identified.

20 Claims, 9 Drawing Sheets

(56) References Cited

U.S. PATENT DOCUMENTS

| | | | |
|---|---|---|---|
| 9,384,565 B2 | 7/2016 | Schoening | |
| 2007/0152804 A1* | 7/2007 | Breed | B60N 2/2863 340/435 |
| 2011/0098898 A1* | 4/2011 | Stahlin | G08G 1/095 701/70 |
| 2011/0229023 A1* | 9/2011 | Jones | G06T 11/001 382/162 |
| 2014/0362195 A1* | 12/2014 | Ng-Thow-Hing | G06K 9/00791 348/51 |
| 2015/0206432 A1* | 7/2015 | Kuehne | G02B 27/017 345/8 |
| 2015/0294505 A1* | 10/2015 | Atsmon | G06T 19/006 345/633 |
| 2016/0363997 A1* | 12/2016 | Black | G06F 3/014 |
| 2018/0005525 A1* | 1/2018 | Parundekar | G08G 1/0967 |
| 2018/0113472 A1* | 4/2018 | Sakr | G05D 1/0276 |
| 2018/0144549 A1* | 5/2018 | Gonzalez | G02B 27/0101 |

FOREIGN PATENT DOCUMENTS

| | | |
|---|---|---|
| JP | 2012-121527 | 6/2012 |
| JP | PO2016-058092 | 4/2016 |
| WO | 2016174882 | 11/2016 |

OTHER PUBLICATIONS

JPO, Notice of Reason for Rejection for Japanese Patent Application No. 2018-119182, Oct. 15, 2019, 3 pages.

* cited by examiner

AUGMENTED REALITY VEHICULAR ASSISTANCE FOR COLOR BLINDNESS

BACKGROUND

The specification relates to augmented reality for providing augmented reality vehicular assistance for drivers who are colorblind.

Color blindness, also known as color vision deficiency, is the decreased ability to see color or differences in color. Red-green color blindness is the most common form, followed by blue-yellow color blindness and total color blindness. Red-green color blindness affects up to 8% of males and 0.5% of females of Northern European descent. There is no medical cure for color blindness.

The ability to see color also decreases in old age. Being color-blind may make people ineligible for certain jobs in certain countries. For example, in some countries people who are colorblind are ineligible to work as pilots, train drivers or taxi drivers.

SUMMARY

Described herein is an augmented reality system (herein an "AR system") operable to provide new of different vehicle functionality to a vehicle. Augmented reality may be referred to herein as "AR."

The AR system may be included in a vehicle. The AR system includes an AR headset and one or more AR gloves which are worn by a driver of the vehicle.

Many drivers who suffer from color blindness report difficulty when driving a vehicle. Specifically, these drivers tend to struggle when interpreting (1) traffic signals and (2) the brake lights of other vehicles. For example, a driver with red-green color blindness may sometimes confuse the red and green traffic signal, which unfortunately results in traffic accidents. These drivers are also unable to discern whether or not the brake lights on the vehicle in front of them are on or off. This situation also results in traffic accidents.

The AR system described herein controls the operation of AR hardware (e.g., a heads-up display unit, "HUD," or AR goggles) improves the performance of a vehicle by assisting color-blind drivers to understand and correctly interpret their driving environment when operating the vehicle.

One of the difficulties in designing vehicular systems to assist color-blind drivers is understand that there are various degrees of color blindness, and any vehicular system which attempts to solve the problem of color blindness for vehicular applications must be able to accommodate all degrees of color blindness. In general, existing solutions which attempt to solve the problem of color blindness for vehicular applications are focused on the problem of making displays more accessible to people who suffer from color blindness by detecting lights using sensors and displays. These existing solutions are not adequate because they are unable to accommodate all degrees of color blindness. Some people with a higher degree of color blindness may still have trouble discerning traffic lights even if aided by these existing solutions, and so, in this way these existing solutions are unable to help such drivers to understand or correctly interpret their driving environment when driving a vehicle. By comparison, the AR system described herein is able to assist all colorblind drivers, regardless of their degree of color blindness.

In some embodiments, the AR system is implemented using an onboard vehicle computer, an electronic control unit ("ECU") or some other onboard unit ("OBU") of a vehicle. The AR system is operable to control the operation of one or more of the following elements of the vehicle: (1) an AR headset; and (2) an AR glove. In particular, the AR system operates one or more of the AR headset and AR glove to assist color-blind drivers of the vehicle to correctly understand and interpret traffic signals and brake lights that are located in their driving environment.

The AR headset includes a HUD or AR goggles. In some embodiments, the HUD is a three-dimensional HUD ("3D-HUD") such as the one depicted in FIG. 5. The color-blind driver views their driving environment through the HUD or AR goggles. When this driving environment includes traffic signals or brake lights, AR system generates graphical overlays that graphically depict one or more words that assist the driver to understand and correctly interpret illuminated traffic signals or brake lights within their driving environment. In some embodiments, the words describe the actions that a driver should take based on an illuminated traffic signal or brake light within the driving environment. In some embodiments, it is preferred that the number of words used be minimized so that the instruction provided by the graphical overlay can be quickly understood by the driver.

In an example for traffic signals, in some embodiments the AR system detects the location of the illuminated traffic light on the HUD or AR goggles using a combination of GPS information and image detection algorithms, and then causes the AR headset to display a graphical overlay depicting the words "GO" for green lights, "DECELERATE" for yellow lights, and "STOP" for red lights. See, for example, FIGS. 4A-4E.

In an example for brake lights, in some embodiments the AR system detects the location of one or more illuminated brake lights of a second vehicle traveling in front of the driver's vehicle using depth sensors and image detection algorithms, and then causes the AR headset to display a graphical overlay depicting the word "BRAKE" when the brake lights of the second vehicle are illuminated. When the brake lights of the second vehicle are not illuminated, the graphical overlay is not depicted by the AR headset. See, e.g., FIG. 4E.

In some embodiments, the AR system identifies one or more and points of interest present for this geographic location which will be difficult for the driver to understand because of their color blindness. For example, the AR system identifies one or more illuminated traffic signals or brake lights.

In some embodiments, the AR system identifies the one or more points of interest using one or more of the following types of digital data: one or more onboard vehicle sensors which detects the presence of the point of interest as well as its range from the vehicle which includes the AR system and generates environment data that describes the presence of the point of interest and its range from the vehicle; geographical positioning system ("GPS") data describing a geographical location of the vehicle which includes the AR system; GPS data describing a geographical location of a point of interest (e.g., which may be transmitted to the AR system via Dedicated Short Range Communication ("DSRC") wireless messaging or some other wireless messaging protocol); and a light data structure which includes digital data that describes the geographical location of static points of interest such as traffic signals and traffic signs which can be queried or cross-referenced using the GPS data for the vehicle to identify whether the vehicle is near a point of interest described by the digital data stored in the light data structure.

In some embodiments, the AR system generates graphical data for causing the AR headset to display one or more graphical overlays for the one or more points of interest. The one or more graphical overlays are configured by the AR system to specifically mitigate the driver's color-blindness. The AR system provides the graphical data to the AR goggles (or, in some embodiments, a HUD or a 3D-HUD) to cause them to display the one or more graphical overlays. See, e.g., FIGS. 4A-4E. Our research indicates that the AR system drastically improves the driving experience and safety for drivers with color blindness, and that the AR system works for all degrees of color-blindness because of its use of words which concisely describe what vehicular actions the driver should take to respond to an otherwise unseen illuminated color in their driving environment.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method for a vehicle including an AR headset, the method including: identifying an illuminated light in a driving environment of the vehicle; determining a vehicular action to be taken responsive to the illuminated light being identified in the driving environment of the vehicle; and displaying an AR overlay using the AR headset that visually depicts a word which describes the vehicular action to be taken responsive to the illuminated light being identified. Other embodiments of this aspect include corresponding computer systems, apparatus, and computer programs recorded on one or more computer storage devices, each configured to perform the actions of the methods.

Implementations may include one or more of the following features. The method where the illuminated light is selected from a group that includes the following: a red light of a traffic signal; a red light of a brake light; a yellow light of a traffic signal; and a green light of a traffic signal. The method where the word is selected from a group that includes the following: stop for a red light of a traffic signal; brake for a red light of a brake light; decelerate for a yellow light of a traffic signal; and go for a green light of a traffic signal. The method where the illuminated light is identified based on digital data included in a dedicated short range communication message received by the vehicle, where the digital data describes the illuminated light. The method where the AR headset is a three-dimensional heads-up display unit which is operable to display the AR overlay so that it visually appears to have three dimensions in a real-world. The method where the AR headset is an AR goggle. The method where the AR overlay consists of text for one word which describes the vehicular action. The method where the method is executed in real time relative to the illuminated light being identified. Implementations of the described techniques may include hardware, a method or process, or computer software on a computer-accessible medium.

One general aspect includes a system of a vehicle including: an AR headset; and an onboard vehicle computer system that is communicatively coupled to the AR headset, the onboard vehicle computer system including a non-transitory memory storing computer code which, when executed by the onboard vehicle computer system causes the onboard vehicle computer system to: identify an illuminated light in a driving environment of the vehicle; determine a vehicular action to be taken responsive to the illuminated light being identified in the driving environment of the vehicle; and cause the AR headset to display an AR overlay that visually depicts a word which describes the vehicular action to be taken responsive to the illuminated light being identified. Other embodiments of this aspect include corresponding computer systems, apparatus, and computer programs recorded on one or more computer storage devices, each configured to perform the actions of the methods.

Implementations may include one or more of the following features. The system where the illuminated light is identified based on measurements of the driving environment recorded by one or more onboard sensors of the vehicle. The system where the illuminated light is identified based on digital data included in a dedicated short range communication message received by the vehicle, where the digital data describes the illuminated light. The system where the AR headset is a three-dimensional heads-up display unit which is operable to display the AR overlay so that it visually appears to have three dimensions in a real-world. The system where the AR headset is an AR goggle. The system where the AR overlay consists of text for one word which describes the vehicular action. The system where the AR overlay is displayed in real time relative to the illuminated light being identified. Implementations of the described techniques may include hardware, a method or process, or computer software on a computer-accessible medium.

One general aspect includes a computer program product including a non-transitory memory of an onboard vehicle computer system of a vehicle storing computer-executable code that, when executed by the onboard vehicle computer system, causes the onboard vehicle computer system to: identify an illuminated light in a driving environment of the vehicle; determine a vehicular action to be taken responsive to the illuminated light being identified in the driving environment of the vehicle; and display an AR overlay on an AR headset of the vehicle that visually depicts a word which describes the vehicular action to be taken responsive to the illuminated light being identified. Other embodiments of this aspect include corresponding computer systems, apparatus, and computer programs recorded on one or more computer storage devices, each configured to perform the actions of the methods.

Implementations may include one or more of the following features. The computer program product where the illuminated light is identified based on measurements of the driving environment recorded by one or more onboard sensors of the vehicle. The computer program product where the illuminated light is identified based on digital data included in a dedicated short range communication message received by the vehicle, where the digital data describes the illuminated light. The computer program product where the AR headset is a three-dimensional heads-up display unit which is operable to display the AR overlay so that it visually appears to have three dimensions in a real-world. The computer program product where the AR overlay consists of text for one word which describes the vehicular action. Implementations of the described techniques may include hardware, a method or process, or computer software on a computer-accessible medium.

BRIEF DESCRIPTION OF THE DRAWINGS

The disclosure is illustrated by way of example, and not by way of limitation in the figures of the accompanying drawings in which like reference numerals are used to refer to similar elements.

DETAILED DESCRIPTION

AR and virtual reality ("VR") are not the same thing. In VR, a user is wearing a VR headset which does not allow the use to see the outside world and a pair of headphones that provide audio that correspond to the images displayed by the VR headset while also canceling out the sound of the real-world. In other words, the purpose of VR is to immerse the user in a VR world so that they forget about the real-world entirely.

Accordingly, VR is not suitable for deployment in vehicles since it distracts the driver from the roadway present in the real-world, and so, it is a safety hazard for this reason. The AR system and the AR manager do not provide a VR experience to a driver because doing so would be life-risking safety hazard.

In AR, a user is wearing an AR headset which includes transparent glass (or plastic or some other suitable transparent material) which is configured to allow the user to see the real-world when looking through the AR headset. The AR headset displays virtual objects which include graphical images that overlay the real-world. The virtual objects may visually appear transparent, translucent, opaque or solid. The virtual objects enhance or modify the way the real-world looks when viewed through the AR headset. The user may also be wearing a AR glove which enhances or modifies the way the real-world feels. In other words, the purpose of AR is to add experiences to the real-world without causing the user to forget about the real-world entirely since the real-world is a part of the AR experience.

Described herein are embodiments of a system of a vehicle that assists a color-blind driver to understand and correctly interpret their driving environment through the use of AR.

Example Overview

Figure 1:
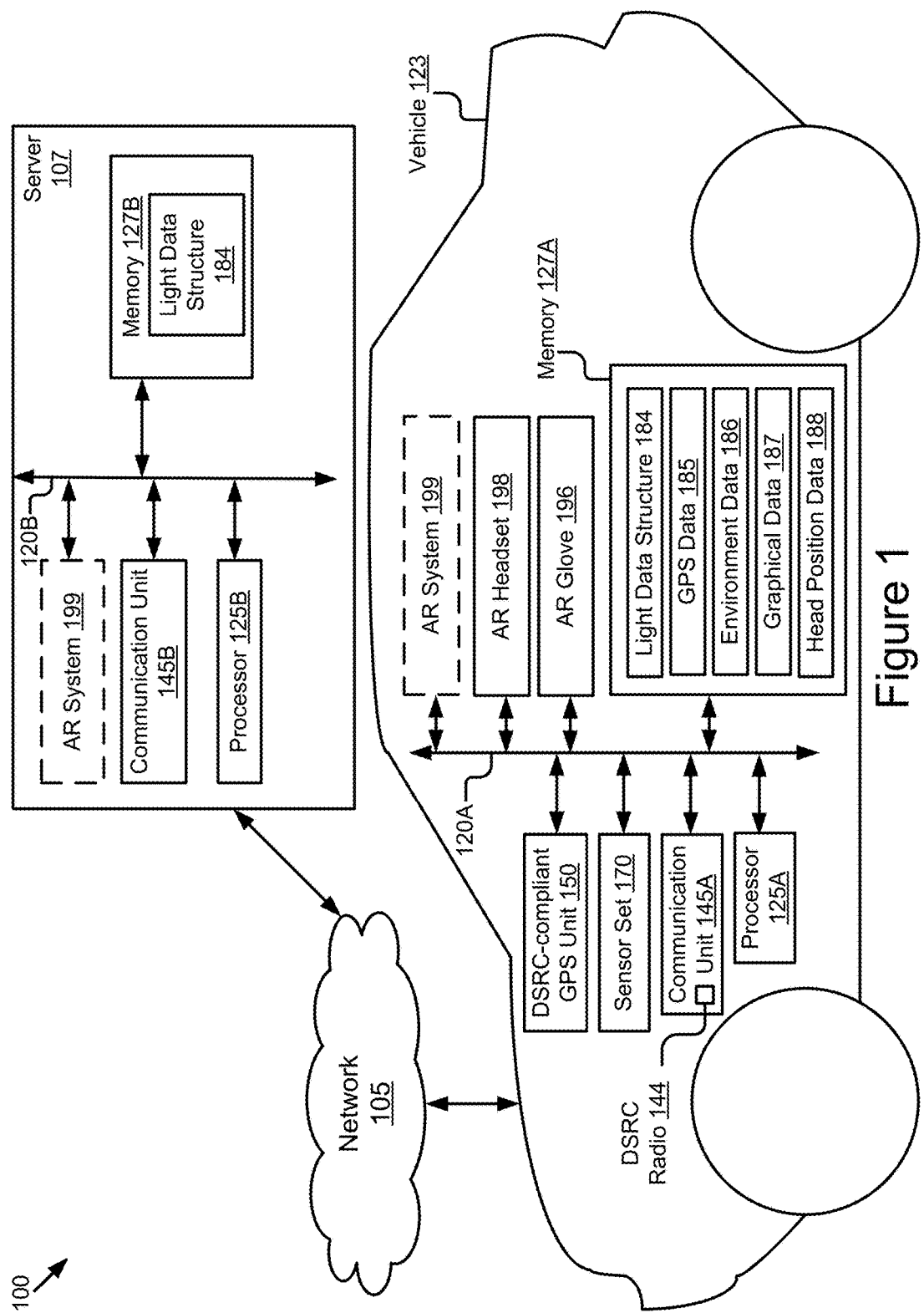
FIG. 1 is a block diagram illustrating an operating environment for a AR system of a vehicle according to some embodiments.

Referring to FIG. 1, depicted is an operating environment 100 for a AR system 199 of a vehicle 123 according to some embodiments. The operating environment 100 may include one or more of the vehicle 123 and a server 107. These elements may be communicatively coupled to one another via a network 105. Although one vehicle 123, one server 107 and one network 105 are depicted in FIG. 1, in practice the operating environment 100 may include one or more vehicles 123, one or more servers 107 and one or more networks 105.

In some embodiments, the vehicle 123 is referred to as an "ego vehicle" because the vehicle 123 includes the AR system 199. For example, in some embodiments, the AR system 199 assists a driver of the vehicle 123 to see and correctly interpret the brake lights of a second vehicle traveling in front of the vehicle 123 (see, e.g., FIG. 4E), and in these embodiments the vehicle 123 may be referred to as an ego vehicle in order to distinguish it from the second vehicle traveling in front of the ego vehicle.

The AR system 199 is depicted with a dashed line in FIG. 1 as an element of the server 107 and the vehicle 123. This is because in some embodiments the functionality of the AR system 199 is distributed across a plurality of endpoints such as the server 107 and the vehicle 123. For example, in some embodiments the light data structure 184 is an element of the server 107 and the functionality of the AR system 199 related to the light data structure 184 is provided by the server 107 since, for example, the server 107 may have more computing power than the vehicle 123.

In some embodiments, the server 107 is an optional feature of the operating environment 100. For example, in some embodiments the AR system 199 of the vehicle 123 is operable to provide all the functionality of the AR system 199 without the use of the server 107. For example, in some embodiments the light data structure 184 is an element of the vehicle 123 and the AR system 199 of the vehicle 123 provides the functionality of the AR system relating to the light data structure 184.

The network 105 may be a conventional type, wired or wireless, and may have numerous different configurations including a star configuration, token ring configuration, or other configurations. Furthermore, the network 105 may include a local area network (LAN), a wide area network (WAN) (e.g., the Internet), or other interconnected data paths across which multiple devices and/or entities may communicate. In some embodiments, the network 105 may include a peer-to-peer network. The network 105 may also be coupled to or may include portions of a telecommunications network for sending data in a variety of different communication protocols. In some embodiments, the network 105 includes Bluetooth® communication networks or a cellular communications network for sending and receiving data including via short messaging service (SMS), multimedia messaging service (MMS), hypertext transfer protocol (HTTP), direct data connection, wireless application protocol (WAP), e-mail, DSRC, full-duplex wireless communication, etc. The network 105 may also include a mobile data network that may include 3G, 4G, LTE, LTE-V2X, VoLTE or any other mobile data network or combination of mobile data networks. Further, the network 105 may include one or more IEEE 802.11 wireless networks.

In some embodiments, the vehicle 123 is a DSRC-equipped vehicle. In some embodiments, a DSRC-equipped vehicle is a vehicle which includes a DSRC radio 144 and a DSRC-compliant GPS unit 150. The DSRC radio 144 is an electronic hardware devices that includes a DSRC transmitter and a DSRC receiver that are licensed to lawfully send and receive DSRC messages on the 5.9 GHz band in the jurisdiction where the DSRC-equipped vehicle is located.

A DSRC message is a wireless message that is specially configured to be send and received by highly mobile devices such as vehicles, and is compliant with one or more of the following DSRC standards, including any derivative or fork thereof: EN 12253:2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); and EN 13372:2004 Dedicated Short-Range Communication (DSRC)—DSRC profiles for RTTT applications (review); EN ISO 14906:2004 Electronic Fee Collection—Application interface.

In the United States, Europe and Asia, DSRC messages are transmitted at 5.9 GHz. In the United States, DSRC messages are allocated 75 MHz of spectrum in the 5.9 GHz band. In Europe and Asia, DSRC messages are allocated 30 MHz of spectrum in the 5.9 GHz band. A wireless message, therefore, is not a DSRC message unless it operates in the 5.9 GHz band. A wireless message is also not a DSRC message unless it is transmitted by a DSRC transmitter of a DSRC radio.

Accordingly, a DSRC message is not any of the following: a WiFi message; a 3G message; a 4G message; an LTE message; a millimeter wave communication message; a Bluetooth message; a satellite communication; and a short-range radio message transmitted or broadcast by a key fob at 315 MHz or 433.92 MHz. For example, in the United States, key fobs for remote keyless systems include a short-range radio transmitter which operates at 315 MHz, and transmissions or broadcasts from this short-range radio transmitter are not DSRC messages since, for example, such transmissions or broadcasts do not comply with any DSRC standard, are not transmitted by a DSRC transmitter of a DSRC radio and are not transmitted at 5.9 GHz. In another example, in Europe and Asia, key fobs for remote keyless systems include a short-range radio transmitter which operates at 433.92 MHz, and transmissions or broadcasts from this short-range radio transmitter are not DSRC messages for similar reasons as those described above for remote keyless systems in the United States.

In some embodiments, a DSRC-equipped vehicle does not include a conventional global positioning system unit ("GPS unit"), and instead includes a DSRC-compliant GPS unit 150. A conventional GPS unit provides positional information that describes a position of the conventional GPS unit with an accuracy of plus or minus 10 meters of the actual position of the conventional GPS unit. By comparison, a DSRC-compliant GPS unit 150 provides GPS data 185 that describes a position of the DSRC-compliant GPS unit 150 with an accuracy of plus or minus 1.5 meters of the actual position of the DSRC-compliant GPS unit 150. This degree of accuracy is referred to as "lane-level accuracy" since, for example, a lane of a roadway is generally about 3 meters wide, and an accuracy of plus or minus 1.5 meters is sufficient to identify which lane the vehicle 123 is traveling in even when the vehicle 123 is traveling in a roadway having a plurality of lanes with traffic flowing in the same direction.

In some embodiments, the DSRC-compliant GPS unit 150 is operable to identify, monitor and track its two-dimensional position within 1.5 meters of its actual position 68% of the time under an open sky. Since lanes of a roadway are typically no less than 3 meters wide, whenever the two-dimensional error of the GPS data 185 is less than 1.5 meters the AR system 199 described herein may analyze the GPS data 185 provided by the DSRC-compliant GPS unit 150 and determine what lane of the roadway the vehicle 123 is traveling in based on the relative positions of a plurality of vehicles on the roadway where the vehicle 123 is included in the plurality.

One example of a DSRC message is a Basic Safety Message ("BSM message"). The DSRC radio 144 of the vehicle 123 transmits BSM messages at regular intervals (e.g., once every 0.1 seconds or some other interval which is user configurable). Each BSM message includes BSM data that describes the vehicle which broadcasted the BSM message. The BSM data is digital data that describes, among other things, a unique identifier of the vehicle which broadcasted the BSM message and the GPS data 185 for that vehicle. In this way the individual vehicles of a plurality of DSRC-equipped vehicles traveling on the roadway can automatically identify themselves to other DSRC-equipped vehicles and inform them of their geographic location with lane-level accuracy. The AR system 199 described herein may use this information, for example, to identify the presence of brake lights and whether their range to the vehicle 123 makes them a point of interest for the driver of the vehicle 123.

In some embodiments, roadside equipment such as traffic signals include a DSRC radio 144 these traffic signals may transmit DSRC messages that include digital data describing their geographic location and, optionally, information indicating which light of the traffic signal is presently illuminated (whether it be the red light, yellow light or the green light). The AR system 199 described herein receives this DSRC message, extracts the digital data and causes the AR headset 198 to depict a graphical overlay that corresponds to the illuminated light of the traffic signal as described by the digital data extracted from the DSRC message.

The network 105 may include one or more communication channels shared among the vehicle 123 and other vehicles on the roadway. The communication channel may include DSRC, LTE-V2X, full-duplex wireless communication or any other wireless communication protocol. For example, the network 105 may be used to transmit a DSRC message, a DSRC probe, a BSM or a full-duplex message including any of the data described herein.

The vehicle 123 is any type of vehicle. For example, the vehicle 123 is one of the following types of vehicles: a car; a truck; a sports utility vehicle; a bus; a semi-truck; a drone or any other roadway-based conveyance.

In some embodiments, the vehicle 123 is an autonomous vehicle or a semi-autonomous vehicle.

In some embodiments, the vehicle 123 includes one or more of the following elements: a processor 125A; a memory 127A; a communication unit 145A including the DSRC radio 144; an AR headset 198; one or more AR gloves 196; and an AR system 199. These elements of the vehicle 123 are communicatively coupled to one another via a bus 120A.

The server 107 is a processor-based computing device. For example, the server 107 may include one or more of the following types of processor-based computing devices: a personal computer; a laptop; a mainframe; or any other processor-based computing device that is operable to function as a server. The server 107 may include a hardware server.

In some embodiments, the server 107 includes one or more of the following elements: a processor 125B; a memory 127B; a communication unit 145B; and an AR system 199. These elements of the server 107 are communicatively coupled to one another via a bus 120B.

The processor 125A of the vehicle 123 and the processor 125B of the server 107 may be referred to herein collectively or individually as the "processor 125" since, for example, the processor 125A of the vehicle 123 provides similar functionality to the components of the vehicle 123 as does the processor 125B of the server 107. For similar reasons, the description provided herein uses the following terms when referring to elements that are common to the vehicle 123 and the server 107: the "memory 127" when referring to the memory 127A and the memory 127B, collectively or individually; and the "communication unit 145" when referring to the communication unit 145A and the communication unit 145B, collectively or individually.

The vehicle 123 and the server 107 are now described.

Vehicle 123

In some embodiments, the processor 125 and the memory 127 are elements of an onboard vehicle computer system (such as computer system 200 described below with reference to FIG. 2). The onboard vehicle computer system is operable to cause or control the operation of the AR system 199. The onboard vehicle computer system is operable to access and execute the data stored on the memory 127 to provide the functionality described herein for the AR system 199 or its elements (see, e.g., FIG. 2). The onboard vehicle computer system is operable execute the AR system 199 which causes the onboard vehicle computer system to execute one or more of the steps of the method 300 described below with reference to FIG. 3.

The processor 125 includes an arithmetic logic unit, a microprocessor, a general-purpose controller, or some other processor array to perform computations and provide electronic display signals to a display device. The processor 125 processes data signals and may include various computing architectures including a complex instruction set computer (CISC) architecture, a reduced instruction set computer (RISC) architecture, or an architecture implementing a combination of instruction sets. The vehicle 123 may include one or more processors 125. Other processors, operating systems, sensors, displays, and physical configurations may be possible.

The memory 127 stores instructions or data that may accessed and executed by the processor 125. The instructions or data may include code for performing the techniques described herein. The memory 127 may be a dynamic random access memory (DRAM) device, a static random access memory (SRAM) device, flash memory, or some other memory device. In some embodiments, the memory 127 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis. A portion of the memory 127 may be reserved for use as a buffer or virtual random access memory (virtual RAM). The vehicle 123 may include one or more memories 127.

The memory 127 of the vehicle 123 may store one or more of the following types of digital data: GPS data 185; environment data 186; graphical data 187; and head position data 188. In some embodiments, the memory 127 stores the light data structure 184.

The GPS data 185 is digital data that describes the geographical location of the vehicle 123. In some embodiments, the GPS data 185 describes the geographical location of the vehicle 123 with lane-level accuracy. The GPS data 185 is used by the AR system 199, for example, to identify whether the vehicle 123 is located at a geographic location that includes a traffic signal or a brake light.

In some embodiments, the GPS data 185 includes digital data that describes the geographical location of other DSRC-equipped objects within the driving environment of the vehicle 123 such as other DSRC-equipped vehicles, DSRC-equipped traffic signals or DSRC-equipped traffic signs. In these embodiments, the AR system 199 includes code and routines that are operable, when executed by the processor 125, to cause the processor 125 to determine whether the vehicle 123 is located at a geographic location that includes a traffic signal or a brake light by comparing the geographical location of the vehicle 123 to the geographical location of the other DSRC-equipped objects.

The light data structure 184 is a table, or some other data structure, that includes digital data that describes the latitude and longitude for different traffic lights or traffic signs in a geographic area. The AR system 199 includes code and routines that are operable, when executed by the processor 125, to cause the processor 125 to compare the GPS data 185 to the digital data stored in the light data structure 184 to identify whether the current GPS location for the vehicle 123 corresponds to the location for a traffic light or traffic sign.

The environment data 186 is digital data that describes the driving environment outside of the vehicle 123. In some embodiments, the environment data 186 describes the measurements of one or more external sensors of the sensor set 170. The AR system 199 includes code and routines that are operable, when executed by the processor 125, to cause the processor 125 to analyze the environment data 186 to identify whether the driving environment for the vehicle 123 includes a traffic light or a brake light for another vehicle traveling in front of the vehicle 123.

In some embodiments, the environment data 186 describes one or more points of interest. A point of interest is an object within the driving environment of the vehicle 123 which is illuminated and of a color which is affected by the specific type and degree of color blindness of the driver of the vehicle 123. In some embodiments, the AR system 199 includes code and routines that are operable, when executed by the processor 125, to cause the processor 125 to analyze the environment data 186 (as well as other inputs such as the GPS data 185 and the light data structure 184) to identify one or more points of interest in the current driving environment for the vehicle 123. The AR system 199 may repeat this analysis at regular intervals over time so that the identified points of interest are regularly updated.

The graphical data 187 is digital data that is operable to cause the AR headset 198 to display one or more AR overlays based on the one or more points of interests described by the environment data 186. For example, the graphical data 187 is operable to cause the AR headset 198 to display one or more of the AR overlays depicted in FIGS. 4A-4E.

The head position data 188 is digital data that describes an orientation of the head of the driver of the vehicle 123. In some embodiments, the head position data 188 describes the measurements of one or more internal sensors included in the sensor set 170. For example, the sensor set 170 includes one or more internal cameras which track the head orientation of the driver of the vehicle 123 and the head position data 188 describes the measurements of these sensors. In some embodiments, the AR headset 198 includes one or more accelerometers which track the orientation of the driver's head.

The communication unit 145 transmits and receives data to and from a network 105 or to another communication channel. In some embodiments, the communication unit 145 may include a DSRC transceiver, a DSRC receiver and other hardware or software necessary to make the vehicle 123 (or some other device such as the server 107) a DSRC-enabled device.

In some embodiments, the communication unit 145 includes a port for direct physical connection to the network 105 or to another communication channel. For example, the communication unit 145 includes a USB, SD, CAT-5, or similar port for wired communication with the network 105. In some embodiments, the communication unit 145 includes a wireless transceiver for exchanging data with the network 105 or other communication channels using one or more wireless communication methods, including: IEEE 802.11; IEEE 802.16, BLUETOOTH®; EN ISO 14906:2004 Electronic Fee Collection—Application interface EN 11253: 2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); EN 13372:2004 Dedicated Short-Range Communication (DSRC)—DSRC profiles for RTTT applications (review); the communication method described in U.S. patent application Ser. No. 14/471,387 filed on Aug. 28, 2014 and entitled "Full-Duplex Coordination System"; or another suitable wireless communication method.

In some embodiments, the communication unit 145 includes a full-duplex coordination system as described in U.S. patent application Ser. No. 14/471,387 filed on Aug. 28, 2014 and entitled "Full-Duplex Coordination System," the entirety of which is herein incorporated by reference.

In some embodiments, the communication unit 145 includes a cellular communications transceiver for sending and receiving data over a cellular communications network including via short messaging service (SMS), multimedia messaging service (MMS), hypertext transfer protocol (HTTP), direct data connection, WAP, e-mail, or another suitable type of electronic communication. In some embodiments, the communication unit 145 includes a wired port and a wireless transceiver. The communication unit 145 also provides other conventional connections to the network 105 for distribution of files or media objects using standard network protocols including TCP/IP, HTTP, HTTPS, and SMTP, millimeter wave, DSRC, etc.

In some embodiments, the communication unit 145 includes a DSRC radio 144. The DSRC radio 144 is a hardware unit that includes a DSRC transmitter and a DSRC receiver. The DSRC transmitter is operable to transmit and broadcast DSRC messages over the 5.9 GHz band. The DSRC receiver is operable to receive DSRC messages over the 5.9 GHz band.

In some embodiments, the DSRC radio 144 includes a non-transitory memory which stores digital data that controls the frequency for broadcasting BSM messages. In some embodiments, the non-transitory memory stores a buffered version of the GPS data 185 for the vehicle 123 so that the GPS data 185 for the vehicle 123 is broadcast as an element of the BSM messages which are regularly broadcast by the DSRC radio 144.

In some embodiments, the DSRC radio 144 includes any hardware or software which is necessary to make the vehicle 123 compliant with the DSRC standards. In some embodiments, the DSRC-compliant GPS unit 150 is an element of the DSRC radio 144.

In some embodiments, the DSRC-compliant GPS unit 150 includes any hardware and software necessary to make the vehicle 123 or the DSRC-compliant GPS unit 150 compliant with one or more of the following DSRC standards, including any derivative or fork thereof: EN 12253: 2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); and EN 13372:2004 Dedicated Short-Range Communication (DSRC)—DSRC profiles for RTTT applications (review); EN ISO 14906: 2004 Electronic Fee Collection—Application interface.

In some embodiments, the DSRC-compliant GPS unit 150 is operable to provide GPS data 185 describing the location of the vehicle 123 with lane-level accuracy.

The AR headset 198 is any conventional AR headset, goggles or glasses. Examples of the AR headset 198 may include one or more of the following: Google™ Glass; CastAR; Moverio BT-200; Meta; Vuzix M-100; Laster SeeThru; Icis; Optinvent ORA-S; GlassUP; Atheer One; K-Glass; and Microsoft™ Hololens. The AR headset 198 is configured so that a driver of the vehicle 123 can be focused on the driving experience when operating the vehicle 123.

In some embodiments, the AR headset 198 includes one or more sensors (e.g., accelerometers) which track the orientation of the driver's head and output head position data 188 which describes the orientation of the driver's head. The head position data 188 is used by the AR system 199, for example, to determine when to cause the AR headset 198 to display the AR overlay which describes a point of interest which is in the driver's field of vision (or optionally obfuscated from the driver's field of vision). For example, the AR system 199 includes code and routines that are operable, when executed by the processor 125, to cause the AR headset 198 to display the AR overlay when the driver's head orientation indicates that they are looking at the road in the direction of the point of interest which is described by the AR overlay. For example, the AR system 199 provides the graphical data 187 to the AR headset 198.

In some embodiments, the AR headset 198 is a 3D-HUD. An example of the 3D-HUD is depicted in FIG. 5. For example, a driver of the vehicle 123 may view the 3D-HUD and the 3D-HUD may display one or more virtual overlays such as those depicted in FIGS. 4A-4E.

In some embodiments, the one or more virtual overlays are displayed by the AR headset 198 as three dimensional virtual overlays that appear to the driver to have three dimensions (x, y and z axis) where the horizontal line of the vehicle 123 windshield is the x axis, the vertical line of the windshield is the y axis and the z axis comes through the windshield in the direction of the driver's head and the outside environment of the vehicle 123.

The vehicle 123 may include one or more AR gloves 196. The AR glove 196 is a haptic feedback glove which is configured so that the driver of the vehicle 123 can touch, grasp, and feel the virtual overlays as if they existed in the real-world (see, for example, the virtual overlays depicted in FIGS. 4A-4E).

In some embodiments, the AR glove 196 may provide haptic feedback to a driver in order to notify them of the presence of a virtual overlay newly displayed by the AR system 199.

In some embodiments, one or more sensors of the sensor set 170 may be operable to record data describing a location of the AR glove 196 relative to some other real-world object or a virtual object.

In some embodiments, the AR glove 196 includes force-feedback units (herein "motors") to apply torque to the driver's fingers which is included in the AR glove 196. These motors are operable, when controlled by the AR system 199, to dynamically alter the direction and magnitude of the force caused by the driver's hand/finger motion in order to simulate a specific virtual overlay's stiffness. In this way, the motors of the AR glove 196 provide light resistance when the driver is handling a virtual object that represents a soft object like a leather knob or handle, and heavy resistance when the virtual object is representing a denser object, such as one that would be made of metal in the real-world.

In some embodiments, the AR glove 196 includes other smaller motors that provide haptic vibrations to the driver's fingertips inside the AR glove 196. These haptic vibrations simulate the impact of the driver's finger tapping on a touch interface or running across a textured surface.

In some embodiments, the motors included in the AR glove 196 are sufficiently powerful that they are operable to provide physical feedback that is capable of physically preventing the driver's fingers from penetrating through virtual objects displayed by the AR headset 198.

As described in more detail below, the AR glove 196 may include a non-transitory cache or buffer that temporarily stores data that it receives from the AR system 199.

The sensor set 170 includes one or more sensors that are operable to measure the physical environment outside of the vehicle 123 (i.e. "external sensors"). For example, the sensor set 170 includes one or more sensors that record one or more physical characteristics of the physical environment that is proximate to the vehicle 123 (i.e., the "driving environment"). The memory 127 may store environment data 186 that describes the one or more physical characteristics recorded by the sensor set 170 from the driving environment.

In some embodiments, the environment data 186 may be used by the AR system 199 to confirm or deny the GPS data 185 or other data stored in the memory 127. For example, the GPS data 185 may indicate that the vehicle 123 is located near a particular landmark, and the environment data 186 may include an image that includes the particular landmark, thereby confirming the accuracy of the GPS data 185.

In some embodiments, the sensor set 170 may include one or more of the following vehicle sensors: a camera; a LIDAR sensor; a radar sensor; a laser altimeter; an infrared detector; a motion detector; a thermostat; a sound detector, a carbon monoxide sensor; a carbon dioxide sensor; an oxygen sensor; a mass air flow sensor; an engine coolant temperature sensor; a throttle position sensor; a crank shaft position sensor; an automobile engine sensor; a valve timer; an air-fuel ratio meter; a blind spot meter; a curb feeler; a defect detector; a Hall effect sensor, a manifold absolute pressure sensor; a parking sensor; a radar gun; a speedometer; a speed sensor; a tire-pressure monitoring sensor; a torque sensor; a transmission fluid temperature sensor; a turbine speed sensor (TSS); a variable reluctance sensor; a vehicle speed sensor (VSS); a water sensor; a wheel speed sensor; and any other type of automotive sensor.

In some embodiments, the sensor set 170 includes one or more sensors that are operable to measure the physical environment inside of the vehicle 123 (i.e. "internal sensors"). For example, the sensor set 170 includes one or more sensors that record one or more physical characteristics of the physical environment that is inside the cabin of the vehicle 123. The memory 127 may store head position data 188 that describes the one or more physical characteristics recorded by the sensor set 170 from inside the cabin of the vehicle 123.

In some embodiments, the AR system 199 includes code and routines that are operable, when executed by the processor 125, to cause the processor 125 to execute one or more steps of the method 300 described below with reference to FIG. 3.

In some embodiments, the AR system 199 of the vehicle 123 may be implemented using hardware including a field-programmable gate array ("FPGA") or an application-specific integrated circuit ("ASIC"). In some other embodiments, the AR system 199 may be implemented using a combination of hardware and software. The AR system 199 may be stored in a combination of the devices (e.g., servers or other devices), or in one of the devices.

The AR system 199 is described in more detail below with reference to FIGS. 2-5.

Server 107

In some embodiments, the server 107 is a cloud server that includes one or more of the following elements: the AR system 199; the communication unit 145; the processor 125; and the memory 127.

The following elements of the server 107 are the same or similar to those described above for the vehicle 123, and so, the descriptions of these elements will not be repeated here: the AR system 199; the processor 125; the memory 127; and the communication unit 145.

In some embodiments, the communication unit 145 of the vehicle 123 transmits one or more wireless messages (i.e., one or more "request messages") to the server 107 at regular intervals via the network 105 that include digital data such as the GPS data 185 and the environment data 186 and the AR system 199 of the server 107 determines the graphical data 187 for the vehicle 123 based on these inputs and, optionally, other locally accessible data such as the light data structure 184. The communication unit 145 of the server 107 then transmits the graphical data 187 to the communication unit 145 of the vehicle 123 via the network 105 in a similar fashion to how the one or more request messages were initially received by the vehicle 123.

Figure 2:
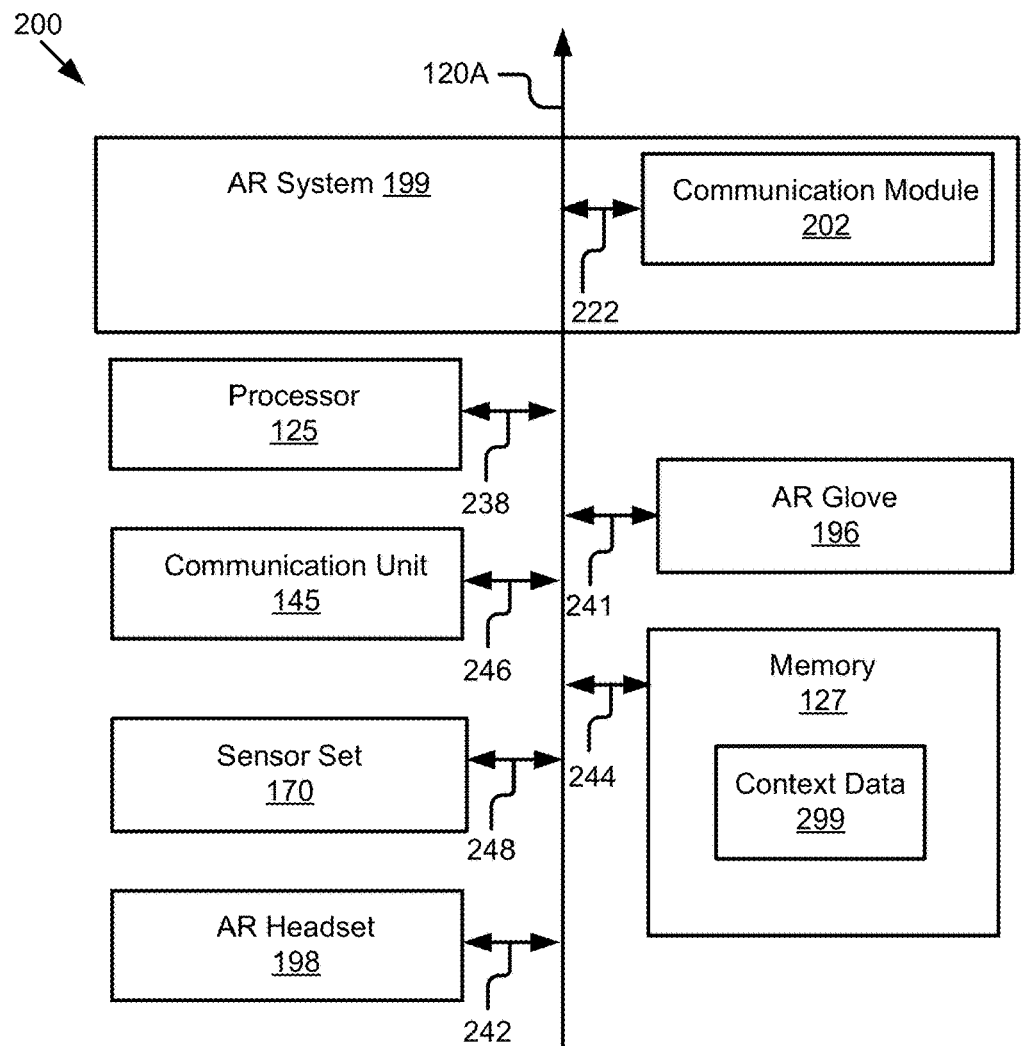
FIG. 2 is a block diagram illustrating an example computer system including the AR system of a vehicle according to some embodiments.

Referring now to FIG. 2, depicted is a block diagram illustrating an example computer system 200 including a AR system 199 according to some embodiments.

In some embodiments, the computer system 200 may include a special-purpose computer system that is programmed to perform one or more steps of a method 300 described below with reference to FIG. 3.

In some embodiments, the computer system 200 may be an element the server 107.

In some embodiments, the computer system 200 may be an onboard vehicle computer of the vehicle 123.

In some embodiments, the computer system 200 may include an electronic control unit, head unit or some other processor-based computing device of the vehicle 123.

The computer system 200 may include one or more of the following elements according to some examples: the AR system 199; the processor 125; the communication unit 145; the sensor set 170; the memory 127; the AR glove 196; and the AR headset 198. The components of the computer system 200 are communicatively coupled by a bus 120.

In the illustrated embodiment, the processor 125 is communicatively coupled to the bus 120 via a signal line 238. The communication unit 145 is communicatively coupled to the bus 120 via a signal line 246. The sensor set 170 is communicatively coupled to the bus 120 via a signal line 248. The AR glove 196 is communicatively coupled to the bus 120 via a signal line 241. The AR headset 198 is communicatively coupled to the bus 120 via a signal line 242. The memory 127 is communicatively coupled to the bus 120 via a signal line 244.

The following elements of the computer system 200 were described above with reference to FIG. 1, and so, those descriptions will not be repeated here: the processor 125; the communication unit 145; the sensor set 170; the AR glove 196; the AR headset 198; and the memory 127.

The memory 127 may store any of the data described above with reference to FIG. 1. The memory 127 may store any data necessary for the computer system 200 to provide its functionality.

In some embodiments, the memory 127 stores context data 299. The context data 299 includes digital data that describes information used by the AR system 199 to analyze the environment data 186 and to identify how to identify and describe a point of present in the real-world based on the environment data 186. For example, the context data 299 is digital data that describes how to identify an illuminated light among other lights which are not illuminated and then determine the color of the illuminated light and what action the driver of the vehicle 123 should take based on the presence of an illuminated light of this particular color being identified.

In one example of the context data 299, if the environment data 186 includes digital data indicating that the illuminated light is green, then the context data 299 includes digital data that describes any information necessary for the AR system 199 to determine that the driver should "GO," and so, the AR system 199 generates graphical data 187 that is operable to cause the AR headset 198 to display a AR overlay with the word "GO" depicted in the AR overlay at a visual location of the AR headset 198 which is correlated to the real-world location of the point of interest (e.g., the green light) as viewed by the driver of the vehicle 123.

In another example of the context data 299, if the environment data 186 includes digital data indicating that the illuminated light is yellow, then the context data 299 includes digital data that describes any information necessary for the AR system 199 to determine that the driver should "DECELERATE," and so, the AR system 199 generates graphical data 187 that is operable to cause the AR headset 198 to display a AR overlay with the word "DECELERATE" depicted in the AR overlay at a visual location of the AR headset 198 which is correlated to the real-world location of the point of interest (e.g., the yellow light) as viewed by the driver of the vehicle 123.

In another example of the context data 299, if the environment data 186 includes digital data indicating that the illuminated light is red and element of a traffic signal or traffic sign, then the context data 299 includes digital data that describes any information necessary for the AR system 199 to determine that the driver should "STOP," and so, the AR system 199 generates graphical data 187 that is operable to cause the AR headset 198 to display a AR overlay with the word "STOP" depicted in the AR overlay at a visual location of the AR headset 198 which is correlated to the real-world location of the point of interest (e.g., the red light of the traffic signal or traffic sign) as viewed by the driver of the vehicle 123.

In another example of the context data 299, if the environment data 186 includes digital data indicating that the illuminated light is red and element of a vehicle (e.g., a brake light), then the context data 299 includes digital data that enables the AR system 199 to know that the driver should "BRAKE," and so, the AR system 199 generates graphical data 187 that is operable to cause the AR headset 198 to display a AR overlay with the word "BRAKE" depicted in the AR overlay at a visual location of the AR headset 198 which is correlated to the real-world location of the point of interest (e.g., the red light of the vehicle) as viewed by the driver of the vehicle 123. Note that the context data 299 differentiates actions among brake lights and stop lights with the words "BRAKE" and "STOP" since, when breaking for brake lights, the driver sometimes slows down but does not stop.

In the illustrated embodiment shown in FIG. 2, the AR system 199 includes a communication module 202. The communication module 202 can be software including routines for handling communications between the AR system 199 and other components of the computer system 200. In some embodiments, the communication module 202 can be a set of instructions executable by the processor 125 to provide the functionality described below for handling communications between the AR system 199 and other components of the computer system 200.

The communication module 202 sends and receives data, via the communication unit 145, to and from one or more elements of the operating environment 100. For example, the communication module 202 receives or transmits, via the communication unit 145, one or more of the following elements: the light data structure 184; the GPS data 185; the environment data 186; the graphical data 187; the head position data 188; and the context data 299. The communication module 202 may send or receive any of the data or messages described above with reference to FIG. 1 or below with reference to FIG. 3 via the communication unit 145.

In some embodiments, the communication module 202 receives data from components of the AR system 199 and stores the data in the memory 127 (or a buffer or cache of the AR glove 196). For example, the communication module 202 receives any of the data described above with reference to the memory 127 from the communication unit 145 (via the network 105) and stores this data in the memory 127 (or a buffer or cache of the AR glove 196).

In some embodiments, the communication module 202 may handle communications between components of the AR system 199.

In some embodiments, the communication module 202 can be stored in the memory 127 of the computer system 200 and can be accessible and executable by the processor 125. The communication module 202 may be adapted for cooperation and communication with the processor 125 and other components of the computer system 200 via signal line 222.

Figure 3:
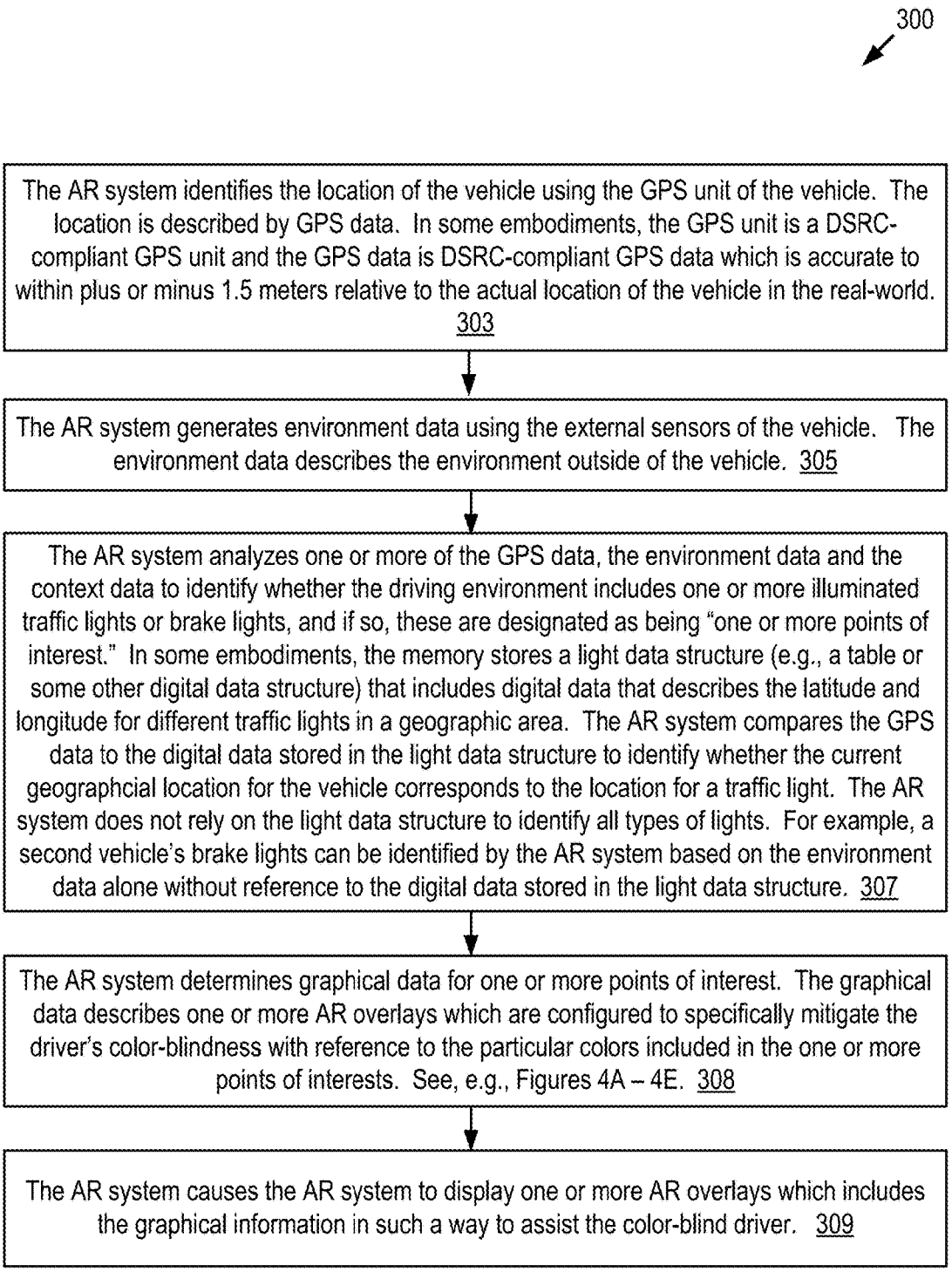
FIG. 3 includes a flowchart of an example method for providing AR-based assistance to a color-blind driver according to some embodiments.

Referring now to FIG. 3, depicted is a flowchart of an example method 300 for providing AR-based assistance to a color-blind driver according to some embodiments.

One or more of the steps described herein for the method 300 may be executed by one or more computer systems 200.

At step 303, the AR system identifies the location of the vehicle using the GPS unit of the vehicle. The location is described by GPS data. In some embodiments, the GPS unit is a DSRC-compliant GPS unit and the GPS data is DSRC-compliant GPS data which is accurate to within plus or minus 1.5 meters relative to the actual location of the vehicle in the real-world.

At step 305, the AR system generates environment data using the external sensors of the vehicle. The environment data describes the environment outside of the vehicle.

At step 307, the AR system analyzes one or more of the GPS data, the environment data and the context data to identify whether the driving environment includes one or more illuminated traffic lights or brake lights, and if so, these are designated as being "one or more points of interest." In some embodiments, the memory stores a light data structure (e.g., a table or some other digital data structure) that includes digital data that describes the latitude and longitude for different traffic lights in a geographic area. The AR system compares the GPS data to the digital data stored in the light data structure to identify whether the current geographical location for the vehicle corresponds to the location for a traffic light. In some embodiments, the AR system does not rely on the light data structure to identify all types of lights. For example, a second vehicle's brake lights can be identified by the AR system based on the environment data alone without reference to the digital data stored in the light data structure.

At step 308, the AR system determines graphical data for one or more points of interest. The graphical data describes one or more AR overlay which are configured to specifically mitigate the driver's color-blindness with reference to the particular colors included in the one or more points of interests.

At step 309, the AR system causes the AR system to display one or more graphical overlays which includes the graphical information in such a way to assist the color-blind driver.

Experimentation shows that the AR system 199 executes the method 300 in real time or near real time relative to the occurrence of an illuminated light in the driving environment of the vehicle.

Referring now to FIGS. 4A-4E, depicted are examples of graphical overlays provided by the AR system according to some embodiments.

Figure 4A:
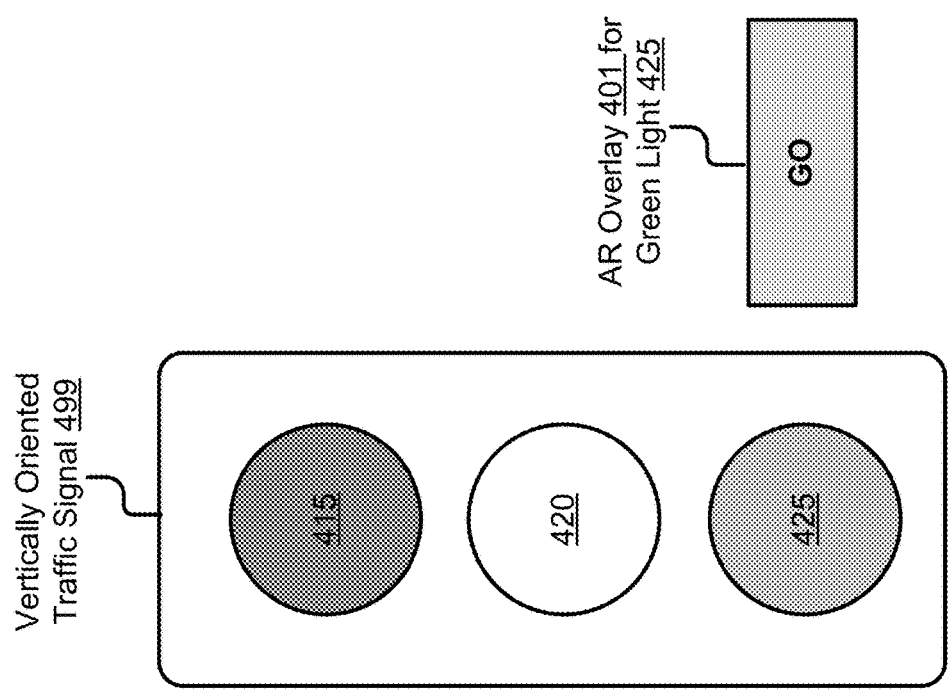
FIGS. 4A-4E are examples of graphical overlays provided by the AR system according to some embodiments.
Figure 5:
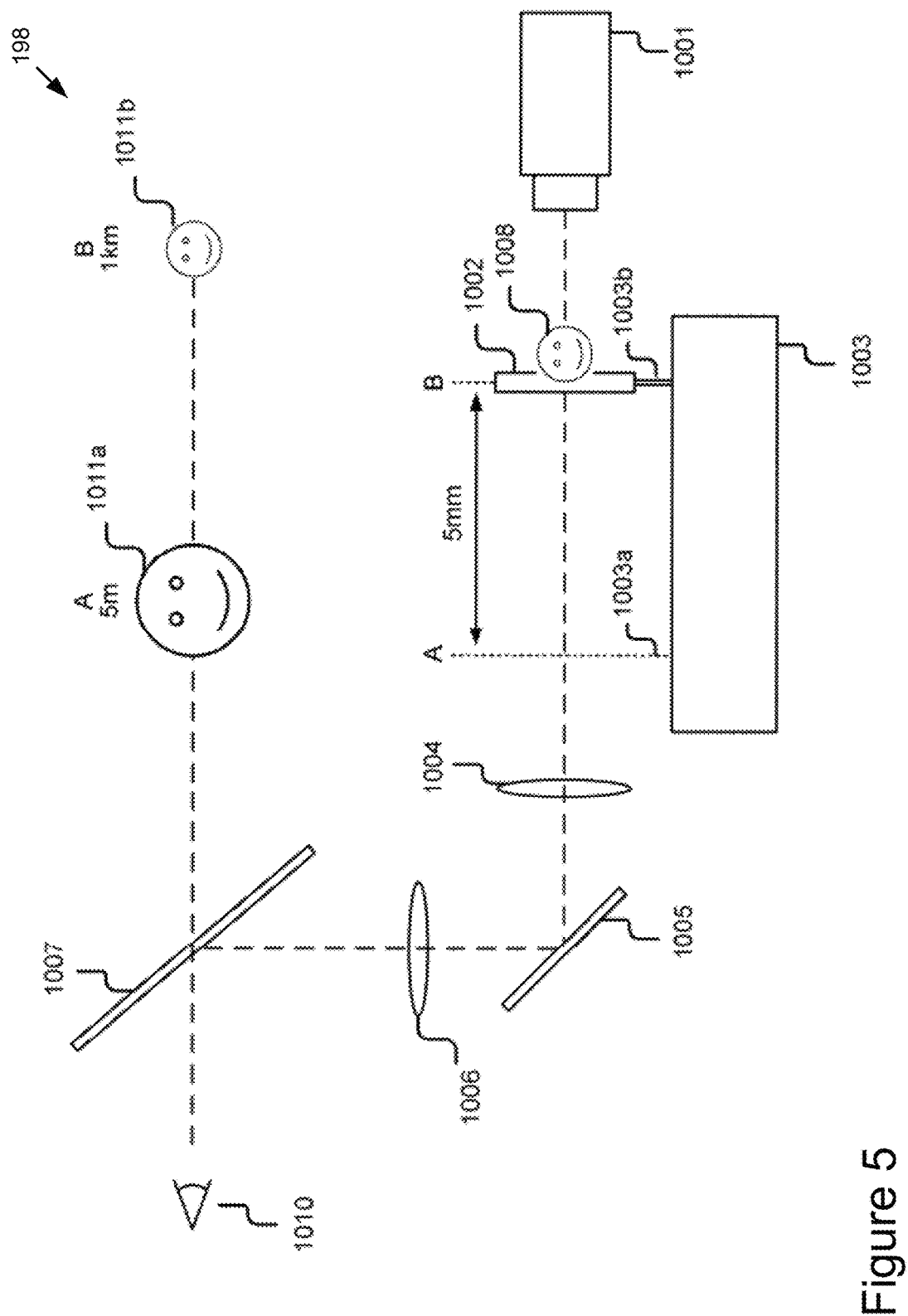
FIG. 5 is a block diagram illustrating an 3D-HUD according to some embodiments.

Referring to FIG. 4A. A vertically oriented traffic signal 499 includes three lights: a red light 415; a yellow light 420; and a green light 425. In FIG. 4A, the environment data 186 indicates that the green light 425 is illuminated. Optionally, a DSRC message transmitted by the vertically oriented traffic signal 499 indicates that the green light 425 is illuminated. The context data 299 describes what action the driver of the vehicle 123 should take, i.e., they should begin driving or continue driving. Accordingly, the AR system 199 generates graphical data 187 that causes the AR headset 198 to depict an AR overlay 401 for the green light 425 which depicts the word "GO," or some other variant for spelling this this word to describe this action (e.g., "Go," "go," etc.).

Figure 4B:
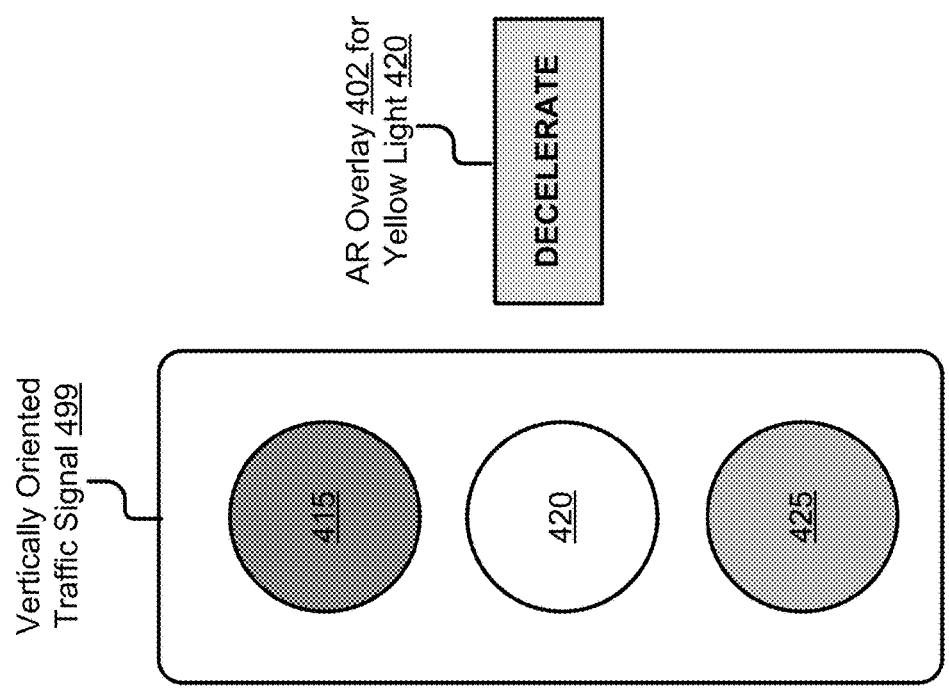

Referring to FIG. 4B. The environment data 186 indicates that the yellow light 420 is illuminated. Optionally, a DSRC message transmitted by the vertically oriented traffic signal 499 indicates that the yellow light 420 is illuminated. The context data 299 describes what action the driver of the vehicle 123 should take, i.e., they should decelerate (i.e., slow down) in preparation for the red light being illuminated. Accordingly, the AR system 199 generates graphical data 187 that causes the AR headset 198 to depict an AR overlay 402 for the yellow light 420 which depicts the word "DECELERATE," or some other variant for spelling this this word to describe this action.

Figure 4C:
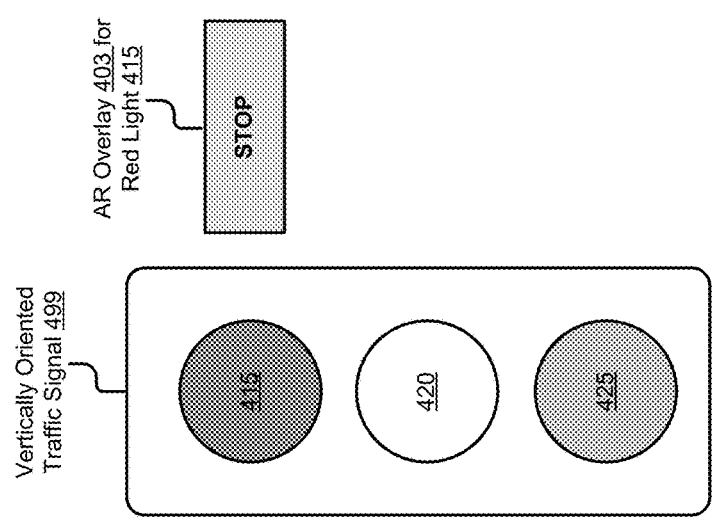

Referring to FIG. 4C. The environment data 186 indicates that the red light 415 is illuminated. Optionally, a DSRC message transmitted by the vertically oriented traffic signal 499 indicates that the red light 415 is illuminated. The context data 299 describes what action the driver of the vehicle 123 should take, i.e., they should stop. Accordingly, the AR system 199 generates graphical data 187 that causes the AR headset 198 to depict an AR overlay 403 for the red light 415 which depicts the word "STOP," or some other variant for spelling this this word to describe this action.

Figure 4D:
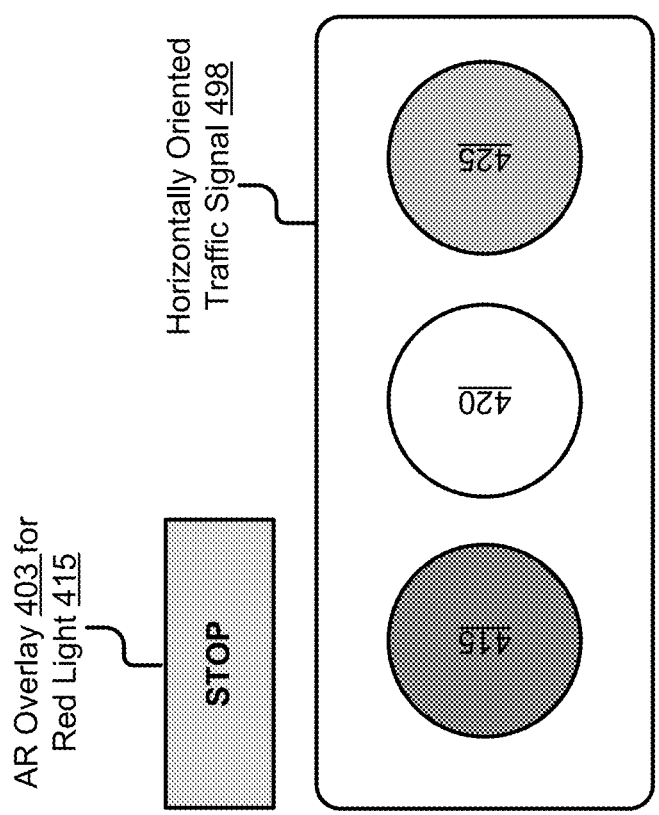

Referring to FIG. 4D. A horizontally oriented traffic signal 498 includes three lights: a red light 415; a yellow light 420; and a green light 425. In FIG. 4D, the environment data 186 indicates that the red light 415 is illuminated. Optionally, a DSRC message transmitted by the horizontally oriented traffic signal 498 indicates that the red light 415 is illuminated. The context data 299 describes what action the driver of the vehicle 123 should take, i.e., they should stop. Accordingly, the AR system 199 generates graphical data 187 that causes the AR headset 198 to depict an AR overlay 403 for the red light 415 which depicts the word "STOP" or some other variant for spelling this this word to describe this action.

Figure 4E:
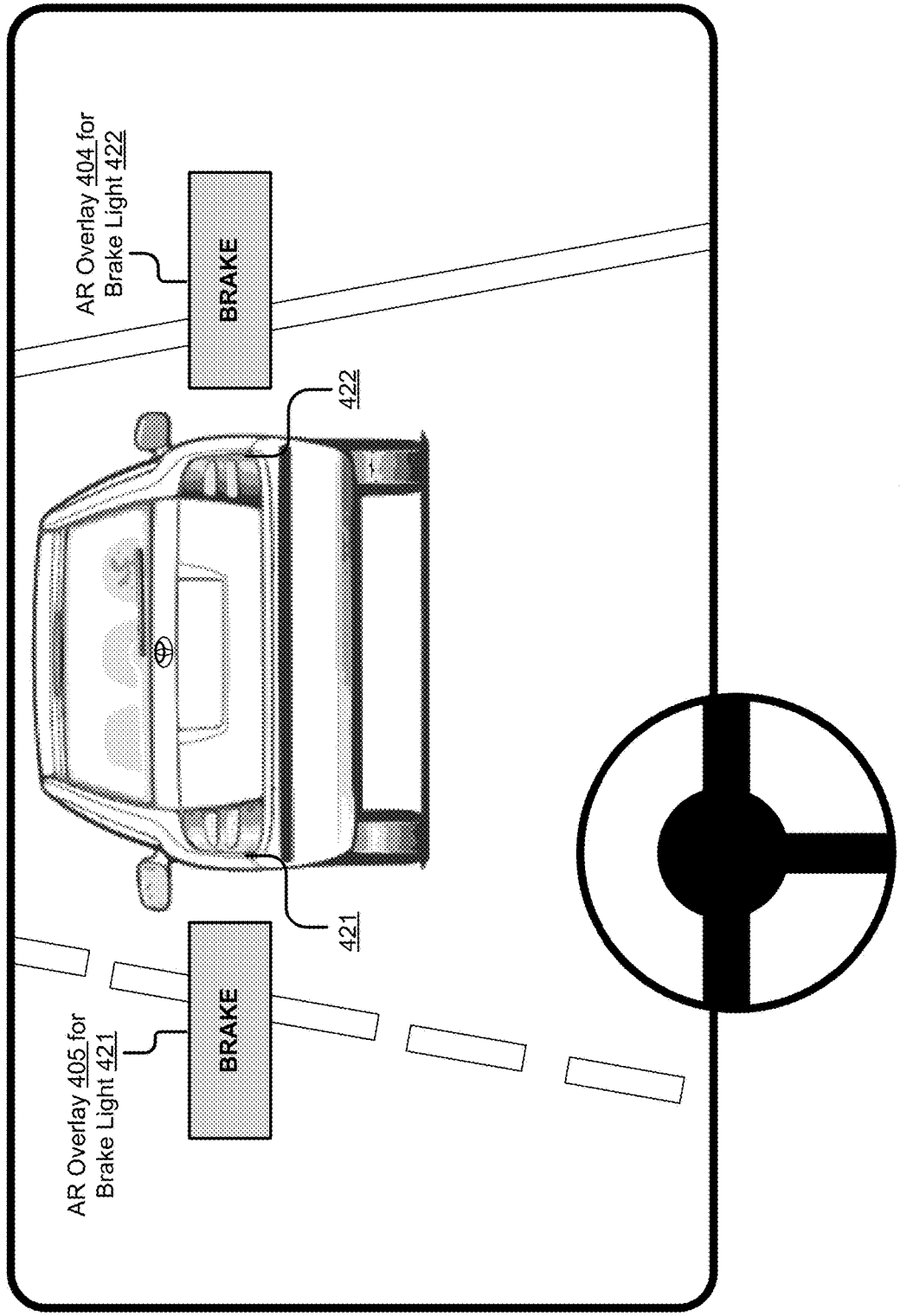

Referring to FIG. 4E. A second vehicle is traveling in front of an ego vehicle. The second vehicle is viewable by the driver of the ego vehicle when looking through a 3D-HUD. The second vehicle includes a first brake light 421 and a second brake light 422. In FIG. 4D, the environment data 186 indicates that the first brake light 421 and the second brake light 422 are illuminated. Optionally, a DSRC message transmitted by the second vehicle indicates that the first brake light 421 and the second brake light 422 are illuminated. The context data 299 describes what action the driver of the vehicle 123 should take, i.e., they should begin braking the ego vehicle. Accordingly, the AR system 199 generates graphical data 187 that causes the 3D-HUD to depict a first AR overlay 405 and a second AR overlay 404 for the first brake light 421 and the second brake light 422, respectively, each of which depicts the word "BRAKE" or some other variant for spelling this this word to describe this action.

Referring to FIG. 5, depicted is a block diagram illustrating a AR headset 198 in embodiments where the AR headset 198 is a 3D-HUD.

In some embodiments, the 3D-HUD includes a projector 1001, a movable screen 1002, a screen-driving unit 1003, an optical system (including lenses 1004, 1006, reflector 1005, etc.). The projector 1001 may be any kind of projector such as a digital mirror device (DMD) project, a liquid crystal projector. The projector 1001 projects an AR overlay 1008 on the movable screen 1002. The AR overlay 1008 may include a virtual object which has three dimensions and visually appears like it exists in the real-world when viewed by the driver of the vehicle. For example, the driver views the AR overlay 1008 and it appears to the driver to be a real-world object, and not an image of a real-world object, which has three dimensions and exists in the same physical reality as the driver.

The movable screen 1002 includes a transparent plate and so the light of the projected image transmits through the movable screen 1002 to be projected on the windshield 1007 of a vehicle (e.g., the vehicle 123). The image projected on the windshield 1007 is perceived by a driver 1010 as if it is a real object (shown as 1011a, 1011b) that exists in the three-dimensional space of the real-world, as opposed to an object that is projected on the windshield.

In some embodiments, the 3D-HUD is capable of controlling the direction of the image relative to the driver 1010 (in other words, the image position in the windshield) by adjusting the projection position on the screen 1002. Further the screen 1002 is movable by the screen-driving unit 1003 in the range between the positions 1003a and 1003b. Adjusting the position of the screen 1002 can vary the depth (distance) of the projected image from the driver 1010 in the real-world. In one example, the movable range of the screen 1002 (distance between positions 1003a and 1003b) may be 5 mm, which correspond to from 5 m away to infinity in the real-world. The use of the 3D-HUD allows the driver 1010 to perceive the projected image exist in the real-world (three-dimensional space). For example, when an image is projected at the same three-dimensional position (or substantially same depth at least) as a real object (such as a pedestrian, car, etc.), the driver does not need to adjust eye focus in order to view the projected image, resulting in easy grasp of the projected image while looking at the real object.

The 3D-HUD depicted in FIG. 5 is provided by way of example. Other examples are possible. These examples may include heads-up displays having more or less complexity than the 3D-HUD depicted in FIG. 5. For example, it is anticipated that in the future there will be heads-up displays that do not require movable parts such as the movable screen 1002. For example, a static screen that does not move may be deployed. The heads-up display deployed may not be a two-dimensional heads-up display unit. In some embodiments, the AR system 199 and the graphical data 187 described above with reference to FIGS. 1-4E is designed to be operable with such components.

In the above description, for purposes of explanation, numerous specific details are set forth in order to provide a thorough understanding of the specification. It will be apparent, however, to one skilled in the art that the disclosure can be practiced without these specific details. In some instances, structures and devices are shown in block diagram form in order to avoid obscuring the description. For example, the present embodiments can be described above primarily with reference to user interfaces and particular hardware. However, the present embodiments can apply to any type of computer system that can receive data and commands, and any peripheral devices providing services.

Reference in the specification to "some embodiments" or "some instances" means that a particular feature, structure, or characteristic described in connection with the embodiments or instances can be included in at least one embodiment of the description. The appearances of the phrase "in some embodiments" in various places in the specification are not necessarily all referring to the same embodiments.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The present embodiments of the specification can also relate to an apparatus for performing the operations herein. This apparatus may be specially constructed for the required purposes, or it may include a general-purpose computer selectively activated or reconfigured by a computer program stored in the computer. Such a computer program may be stored in a computer-readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory, or any type of media suitable for storing electronic instructions, each coupled to a computer system bus.

The specification can take the form of some entirely hardware embodiments, some entirely software embodiments or some embodiments containing both hardware and software elements. In some preferred embodiments, the specification is implemented in software, which includes, but is not limited to, firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A data processing system suitable for storing or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including, but not limited, to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem, and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description of the embodiments of the specification has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies, and other aspects are not mandatory or significant, and the mechanisms that implement the specification or its features may have different names, divisions, or formats. Furthermore, as will be apparent to one of ordinary skill in the relevant art, the modules, routines, features, attributes, methodologies, and other aspects of the disclosure can be implemented as software, hardware, firmware, or any combination of the three. Also, wherever a component, an example of which is a module, of the specification is implemented as software, the component can be implemented as a standalone program, as part of a larger program, as a plurality of separate programs, as a statically or dynamically linked library, as a kernel-loadable module, as a device driver, or in every and any other way known now or in the future to those of ordinary skill in the art of computer programming. Additionally, the disclosure is in no way limited to embodiment in any specific programming language, or for any specific operating system or environment. Accordingly, the disclosure is intended to be illustrative, but not limiting, of the scope of the specification, which is set forth in the following claims.

What is claimed is:

1. A method for a vehicle including an augmented reality ("AR") headset, the method comprising:
    determining a location of the vehicle using a Dedicated Short Range Communication (DSRC)-compliant GPS unit in the vehicle, wherein the location is accurate to within plus or minus 1.5 meters;
    identifying an illuminated light in a driving environment of the vehicle based on the location of the vehicle;
    determining that the illuminated light is a point of interest based on a color of the illuminated light and a driver of the vehicle being affected by a type of color blindness;
    determining a vehicular action to be taken responsive to the illuminated light being identified in the driving environment of the vehicle and the illuminated light being the point of interest;
    receiving head position data from one or more internal cameras of the vehicle, the head position data describing a head orientation of the driver;
    determining based on the head position data that the head orientation of the driver indicates that the point of interest is in a field of vision of the driver; and
    responsive to determining that the point of interest is in the field of vision of the driver, displaying an AR overlay using the AR headset that visually depicts the vehicular action to be taken responsive to the illuminated light being identified.

2. The method of claim 1, further comprising providing haptic feedback in an AR glove to notify the driver of a presence of the AR overlay newly displayed by the AR headset.

3. The method of claim 1, wherein the AR overlay visually depicts a word that is selected from a group that includes the following: "STOP" for a red light of a traffic signal; "BRAKE" for a red light of a brake light; "DECELERATE" for a yellow light of a traffic signal; and "GO" for a green light of a traffic signal.

4. The method of claim 1, wherein the illuminated light is further identified from a Basic Safety Message (BSM) that describes a location of the illuminated light.

5. The method of claim 1, wherein the AR headset is a three-dimensional heads-up display unit which is operable to display the AR overlay so that it visually appears to have three dimensions in a real-world.

6. The method of claim 1, wherein the AR headset is an AR goggle.

7. The method of claim 1, wherein the AR overlay consists of text for one word which describes the vehicular action.

8. The method of claim 1, wherein the method is executed in real time relative to the illuminated light being identified.

9. A system of a vehicle comprising:
    an augmented reality ("AR") headset; and
    an onboard vehicle computer system that is communicatively coupled to the AR headset, the onboard vehicle computer system including a non-transitory memory storing computer code which, when executed by the onboard vehicle computer system causes the onboard vehicle computer system to:
        determine a location of the vehicle using a Dedicated Short Range Communication (DSRC)-compliant GPS unit in the vehicle, wherein the location is accurate to within plus or minus 1.5 meters;
        identify an illuminated light in a driving environment of the vehicle based on the location of the vehicle;
        determine that the illuminated light is a point of interest based on a color of the illuminated light and a driver of the vehicle being affected by a type of color blindness;
        determine a vehicular action to be taken responsive to the illuminated light being identified in the driving environment of the vehicle and the illuminated light being the point of interest;
        receive head position data from one or more internal cameras of the vehicle, the head position data describing a head orientation of the driver;
        determine based on the head position data that the head orientation of the driver indicates that the point of interest is in a field of vision of the driver; and
        responsive to determining that the point of interest is in the field of vision of the driver, cause the AR headset to display an AR overlay that visually depicts the vehicular action to be taken responsive to the illuminated light being identified.

10. The system of claim 9, wherein the illuminated light is identified based on measurements of the driving environment recorded by one or more external cameras of the vehicle.

11. The system of claim 9, wherein the illuminated light is further identified from a Basic Safety Message (BSM) that describes a location of the illuminated light.

12. The system of claim 9, wherein the AR headset is a three-dimensional heads-up display unit which is operable to display the AR overlay so that it visually appears to have three dimensions in a real-world.

13. The system of claim 9, wherein the AR headset is an AR goggle.

14. The system of claim 9, wherein the AR overlay consists of text for one word which describes the vehicular action.

15. The system of claim 9, wherein the AR overlay is displayed in real time relative to the illuminated light being identified.

16. A computer program product comprising a non-transitory memory of an onboard vehicle computer system of a vehicle storing computer-executable code that, when executed by the onboard vehicle computer system, causes the onboard vehicle computer system to:
    determine a location of the vehicle using a Dedicated Short Range Communication (DSRC)-compliant GPS unit in the vehicle, wherein the location is accurate to within plus or minus 1.5 meters;

identify an illuminated light in a driving environment of the vehicle based on the location of the vehicle;

determine that the illuminated light is a point of interest based on a color of the illuminated light and a driver of the vehicle being affected by a type of color blindness;

determine a vehicular action to be taken responsive to the illuminated light being identified in the driving environment of the vehicle and the illuminated light being the point of interest;

receive head position data from one or more internal cameras of the vehicle, the head position data describing a head orientation of the driver;

determine based on the head position data that the head orientation of the driver indicates that the point of interest is in a field of vision of the driver; and responsive to determining that the point of interest is in the field of vision of the driver, display an augmented reality ("AR") overlay on an AR headset of the vehicle that visually depicts the vehicular action to be taken responsive to the illuminated light being identified.

17. The computer program product of claim 16, wherein the illuminated light is identified based on measurements of the driving environment recorded by one or more onboard sensors of the vehicle.

18. The computer program product of claim 16, wherein the illuminated light is further identified from a Basic Safety Message (BSM) that describes a location of the illuminated light.

19. The computer program product of claim 16, wherein the AR headset is a three-dimensional heads-up display unit which is operable to display the AR overlay so that it visually appears to have three dimensions in a real-world.

20. The computer program product of claim 16, wherein the AR overlay consists of text for one word which describes the vehicular action.

* * * * *